(12) United States Patent
Acosta

(10) Patent No.: US 11,819,447 B2
(45) Date of Patent: Nov. 21, 2023

(54) URINE COLLECTION APPARATUSES

(71) Applicant: Acosta Medical Group, INC., Humble, TX (US)

(72) Inventor: Fred Acosta, Humble, TX (US)

(73) Assignee: ACOSTA MEDICAL GROUP, Houston, TX (US)

( * ) Notice: Subject to any disclaimer, the term of this patent is extended or adjusted under 35 U.S.C. 154(b) by 0 days.

(21) Appl. No.: 17/773,272

(22) PCT Filed: Oct. 29, 2020

(86) PCT No.: PCT/US2020/057952
§ 371 (c)(1),
(2) Date: Apr. 29, 2022

(87) PCT Pub. No.: WO2021/087107
PCT Pub. Date: May 6, 2021

(65) Prior Publication Data
US 2023/0129897 A1 Apr. 27, 2023

Related U.S. Application Data

(60) Provisional application No. 62/927,370, filed on Oct. 29, 2019.

(51) Int. Cl.
*A61F 5/455* (2006.01)
*A61F 5/44* (2006.01)

(52) U.S. Cl.
CPC ............ *A61F 5/455* (2013.01); *A61F 5/4405* (2013.01); *A61F 5/4408* (2013.01)

(58) Field of Classification Search
CPC ...... A61F 5/4405; A61F 5/4408; A61F 5/455; A61F 5/4556; A61B 10/007; A61G 9/006; A47K 11/12
See application file for complete search history.

(56) References Cited

U.S. PATENT DOCUMENTS

| | | | |
|---|---|---|---|
| 1,928,170 A * | 9/1933 | Dwork | A61F 5/455 4/144.4 |
| 5,295,983 A | 3/1994 | Kubo | |
| 5,953,763 A * | 9/1999 | Gouget | A47K 11/12 4/144.1 |
| 6,699,174 B1 | 3/2004 | Bennett | |
| 2014/0094665 A1 | 4/2014 | Ron | |
| 2017/0196726 A1 | 7/2017 | SanAntonio | |

OTHER PUBLICATIONS

International Search Report dated Jan. 28, 2021 issued in PCT/US2020/57952.

* cited by examiner

*Primary Examiner* — Erin Deery
(74) *Attorney, Agent, or Firm* — Hunton Andrews Kurth LLP

(57) ABSTRACT

A urine collection device suitable for female or male use. The device may be configured to the wearer and has an open cavity with one or more one way valves through which urine may flow into an enclosed cavity. The enclosed cavity comprises a valve through which collected urine may be expelled so that the device may be reused if desired.

20 Claims, 5 Drawing Sheets

DETAIL A

DETAIL A

URINE COLLECTION APPARATUSES

CROSS-REFERENCE TO RELATED APPLICATIONS

The present application claims priority to U.S. provisional application 62/927,370 filed Oct. 29, 2019. It is also related to WO2019/204465 filed Apr. 17, 2019 and U.S. Pat. No. 10,588,775 issued Mar. 17, 2020 which for U.S. purposes are both incorporated by reference herein.

FIELD OF THE INVENTION

The present invention relates generally to a urine collection device that is suitable for females or males and particularly for those patients with skin breakdown in the penis or vaginal area.

BACKGROUND AND SUMMARY

Incontinence is an ever increasing issue for an aging population. Often, males and females with incontinence problems may use absorbable undergarments, pads, diapers, or other such products designed to absorb urine. Unfortunately, such products are expensive as they have to be frequently replaced. Such products also present disposal and related environmental issues. In addition, such products may also be ill-fitting, uncomfortable, unattractive, and/or present problems such as leakage, rashes, or other skin irritations. What is needed is a urine collection device that is suitable for males or females, is potentially reusable, and/or avoids one or more of the aforementioned disadvantages.

Advantageously, the devices of the present application meet one or more of the aforementioned needs. In one embodiment, the urine collection device comprises an open cavity with a raised wall around the perimeter of the open cavity and a bottom connected to the raised wall. The device also has a closed cavity having an interior. The closed cavity at least partially surrounds the open cavity. The raised wall around the perimeter of the open cavity comprises a wall of the closed cavity. The raised wall comprises one or more one way valves configured for fluid to pass through the open cavity into the interior of the closed cavity. The device comprises a mechanism to secure the device to a user having a female urethal opening or a male having a penis each of which also has a buttocks. The open cavity is configured to sealably encompass the female urethal opening or male penis while the closed cavity is configured to fit between a user's legs and extend at least partially over the buttocks.

Advantageously, this device will work for both female and male hospital patients. The device may further be connected to a bedside drainage device. The device may reduce or eliminate infections even in those patients with high probability for infections and/or poor immunity such as the elderly. In some embodiments at least a portion to all of the perineal space is areated to allow for the body to maintain normal function. Prior art devices typically cover this space which causes medical issues. Keeping space open and areated is much better for a patient with, for example, compromised immunity like the elderly. Thus, in some embodiments area 102 open cavity may have a slit that can be cut to fit around vaginal space so as to allow vagina to be exposed to air and get aeration and/or ventilation.

BRIEF DESCRIPTION OF THE DRAWINGS

So that the manner in which the above recited features, advantages, and objects of the present invention are attained and can be understood in detail, a more particular description of the invention, briefly summarized above, may be had by reference to the embodiments thereof which are illustrated in the appended drawings. It is to be noted, however, that the appended drawings only illustrate preferred embodiments of this invention, and are therefore not to be considered limiting of its scope, for the invention may admit to other equally effective embodiments that vary only in detail. In the drawings.

DESCRIPTION OF THE PREFERRED EMBODIMENTS

Figure 1:
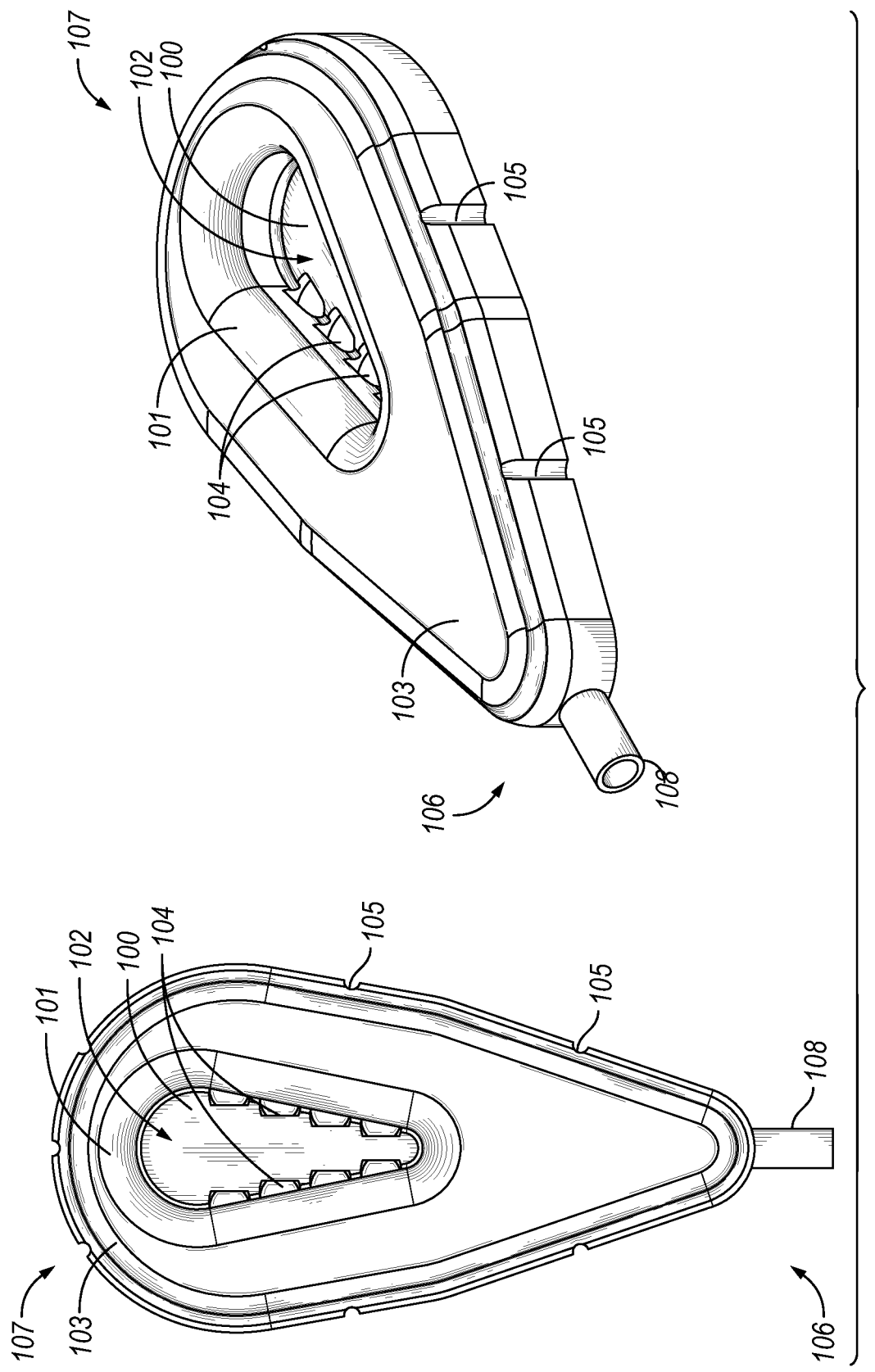
FIG. 1 shows exemplary embodiments of a female urine collection device.

Certain terms are used throughout the following description and claims to refer to particular system components. As one skilled in the art will appreciate, different companies may refer to a component by different names. This document does not intend to distinguish between components that differ in name but not function.

In one embodiment the invention pertains to a urine collection device and preferably to a urine collection device for female users although with modifications it can be configured for a male as described below. The device typically has an open cavity with a raised wall around the perimeter of the open cavity and a bottom connected to the raised wall. The shape of the open cavity may be selected based on a number of factors such as, for example, the size and shape of the intended user, the materials employed, and the desired results. Typically, the shape of the open cavity is somewhat rounded and tapered toward one end which end may in some cases be the portion designed to fit between a user's legs.

The raised wall (and/or the bottom in some embodiments wherein the closed cavity encompasses the bottom) typically comprises one or more one way valves configured for fluid to pass through the open cavity into an interior of a closed cavity. The one or more one way valves also typically prevent passed fluid from returning to the open cavity. These one way valves may be any suitable one way fluid valves that function in the presence of urine and do not hinder the urine from passing to the closed cavity, i.e., urine chamber. In some cases at least a portion up to all of the material of the raised wall or bottom itself may serve as a one way valve in that a material may be selected that allows urine to pass through the material in one direction but not the other. Suitable valves include, for example, check valves, anti reflux valves, no return valves, flutter valves, fluid directing channels, etc.

The number and precise location of the one way fluid valves may vary depending on the size and shape of the intended user, other characteristics of the device, and the desired results. In some embodiments the number of one way valves is two or more, or three or more, or four or more, or five or more, or six or more, or seven or more, or eight or more valves. Alternatively, there may be one long one way valve that at least partially to fully surrounds the perimeter of the base of the open cavity. Another embodiment is that the area attaching over a female's labia majora is elevated to create a downward flow of fluid/urine to inner cavity. In doing so outside walls may create a cupping effect which would hold and with user's movement cause urine to travel down to a one way valve at bottom of open cavity.

In some embodiments the valves are located such that the passage of urine to the closed cavity is facilitated by gravity. Thus, in some embodiments the device may be configured via the number or location of one way valves or in some other manner such that fluid passes through the one or more one way valves into the closed cavity via gravity when a user wearing the device is in an upright position, or a standing position, or a seated position, or a horizontal position facing up, or any combination of the aforementioned positions. Advantageously, in some embodiments the device may be configured via the number or location of one way valves or in some other convenient manner such as cavity shape or size such that fluid passes through the one or more one way valves into the closed cavity via gravity no matter the position of the user.

A closed cavity is operably connected through the one way valve or valves of the device to the open cavity. The closed cavity comprises an interior for the collection of urine through the one way valve or valves. Typically, the closed cavity at least partially surrounds the open cavity and the raised wall around the perimeter of the open cavity comprises a wall, preferably an inner wall, i.e., inner perimeter wall, of the closed cavity. The size of the closed cavity may vary depending upon such parameters as the intended user's size, amount and frequency of urine, and the desired results. In some embodiments, the interior of the closed cavity is configured to hold at least 400, or at least 500 cc of fluid. Generally, in some embodiments it may be advantageous if the specific design of the device does not allow urine to sequestrate in device, but rather, exits the device and flows to a leg or an ankle bag and/or a bedside collection system.

The open cavity is typically configured to sealably encompass or engage the female urethal opening or male penis. In this manner urine does not substantially leak outside the device and instead is transferred to the closed cavity through the one way valves. That is, when a releasable mechanism is engaged to secure the device to a female user the open cavity encompasses the female urethal opening such that urine is captured within the open cavity. In some embodiments, the closed cavity is configured to fit between a user's legs and extend at least partially over the buttocks. Thus, a typical shape of the device may be that of, for example, a tapered ellipse.

The mechanism type and number to secure the device to a user may vary. In some embodiments it is selected from the group consisting of tape, adhesive, straps, velcro, kellum grip, suction cup, or combinations thereof. A kellum grip is a type of suction cupping grip that may extend into vaginal space or urethral isolation. For example, a compressible cup may help anchor device utilizing the inside of vaginal space with use of light suction and combination of all. The device can be used as urine collector port will exist to draw urine sample. The device may have an attached cover to open space to completely seal system.

The number of such mechanisms on a given device may vary but typically both the type and number are selected such that the open cavity may sealably encompass the female urethal opening or male penis such that urine does not substantially leak outside the device. Thus, there may be a number of mechanisms proximate to the perimeter of the closed cavity of the device, e.g., two or more, or three or more, or four or more, or five or more, or six or more, or seven or more, or eight or more mechanisms. The precise location, number, and type of the mechanisms may be optimized to provide for an optimum balance of comfort and sealing of the urethral or penis opening to prevent leakage.

The material for the raised wall, bottom connected to the raised wall, and remainder of the closed cavity may be the same or different material for each. The selected materials may vary depending upon the specific configuration of the device but preferably the same material is employed for a majority or all of the components of the open and closed cavity. The material may be any suitable material so long as it is capable of accepting one way valves and is not substantially degraded or deteriorated by urine. Preferably, at least the material exposed to the user's skin does not significantly irritate human skin and can be worn with reasonable comfort. In some embodiments it may be desirable for the material to have a hydrophobic surface such that it serves as an antimicrobial.

Representative materials that may be employed include, for example, rubbers, latexes, polychloroprenes, nylons, polyethylenes, polypropylenes, elastomers, polyolefins, polyurethanes, epoxies, silicones, sealing wax, honey sponge, and/or other wicking materials.

The cavities of the device comprising the one or more one way valves may be made in any convenient manner which manner may vary depending upon the materials, device configurations, intended user, desired results, and/or available equipment. In some embodiments, a plastic processing method is employed such as a molding process like injection molding, blow molding, extrusion, rotational molding, or some combination thereof. Of course, in some cases a 3D printer could also be employed.

In some embodiments, the device could be configured such that no valves are required and instead the walls are configured to just cup fluid such that, for example, if the device were turned upside down the walls would prevent urine from exiting the device. In some embodiments the walls may be an inflatable chamber that a user or caregiver could fill with air in a convenient manner such as a syringe. This inflatable chamber or air bladder ring can be configured such that fluid would force the ring to float up to prevent fluid from leaking if urine stagnated in inner space or while the patient was turned sideways.

If desired the urine collection device may be provided with a mechanism for emptying the closed cavity of urine so that the device may be re-used. Such a mechanism may be any convenient one and may vary depending upon the configuration and desired results. For example, in some cases it may be desirable to empty the device while it is still in place. In some embodiments the closed cavity comprises a two way valve configured to empty fluid from the closed cavity when the valve is an open position. Of course, other mechanisms may include releasable plug or plugs or various types of drains.

If desired, the device could be expanded to be larger and with a bigger cavity. For example a sheet attaching from hip to hip with air ring surrounding area around pelvis that directs urine to a funneled area between leg further funneled to be able to connect a funnel end to a drainage bedside system.

When attaching the device to a user and, in particular, a female user in some embodiments a base of, for example, a hydrogel material is applied. Such materials may stay on female/male perineum for approximately five to seven days or more. In some embodiments the back side of the device comprises an adhesive with peel backing that would allow the device to adhere to hydrogel material on the user. In other embodiments the peel backing is not required for the device to adhere to the user. The hydrogel material as a dressing may be adhered and taken off many times in some embodiments.

Specific representative devices are described below.

Specific Embodiments

Figure 2:
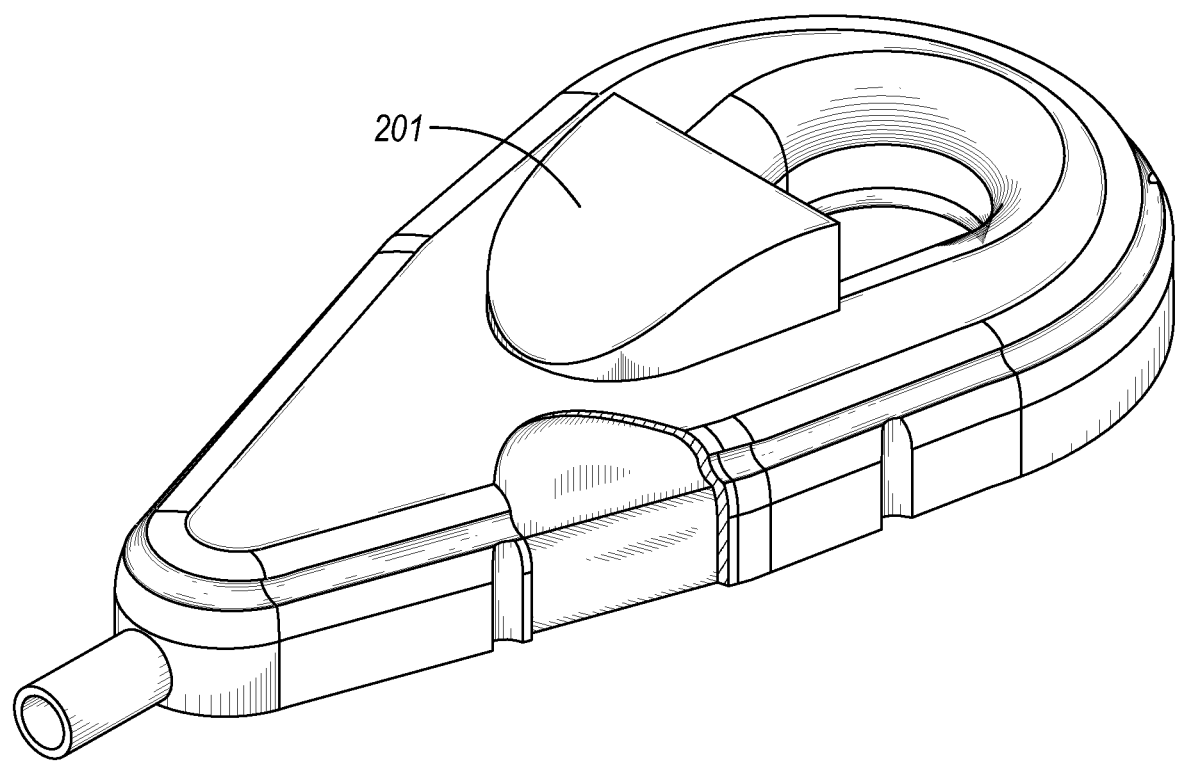
FIG. 2 shows a version of the device suitable for a male user.

FIG. 1 shows a representative device of the present application. 100 is an open cavity with a raised wall 101 around the perimeter of the open cavity and a bottom 102 connected to the raised wall 101. The device has a closed cavity having an interior for urine collection beneath the wall 103 bounded by the common raised wall 101. The closed cavity at least partially surrounds the open cavity 102 and the raised wall 101 around the perimeter of the open cavity comprises a wall of the closed cavity. If desired, a slit opening in 102 allows for adherence to labia majora in females and opening allows for female to urinate into open cavity. Alternatively, a round opening with a sheath may be attached to adhere to base of penis shaft and the male penis would fall into open cavity. and be secured in position via holder or sheath 201 which may act as a "splashguard" as shown in FIG. 2.

Figure 3:
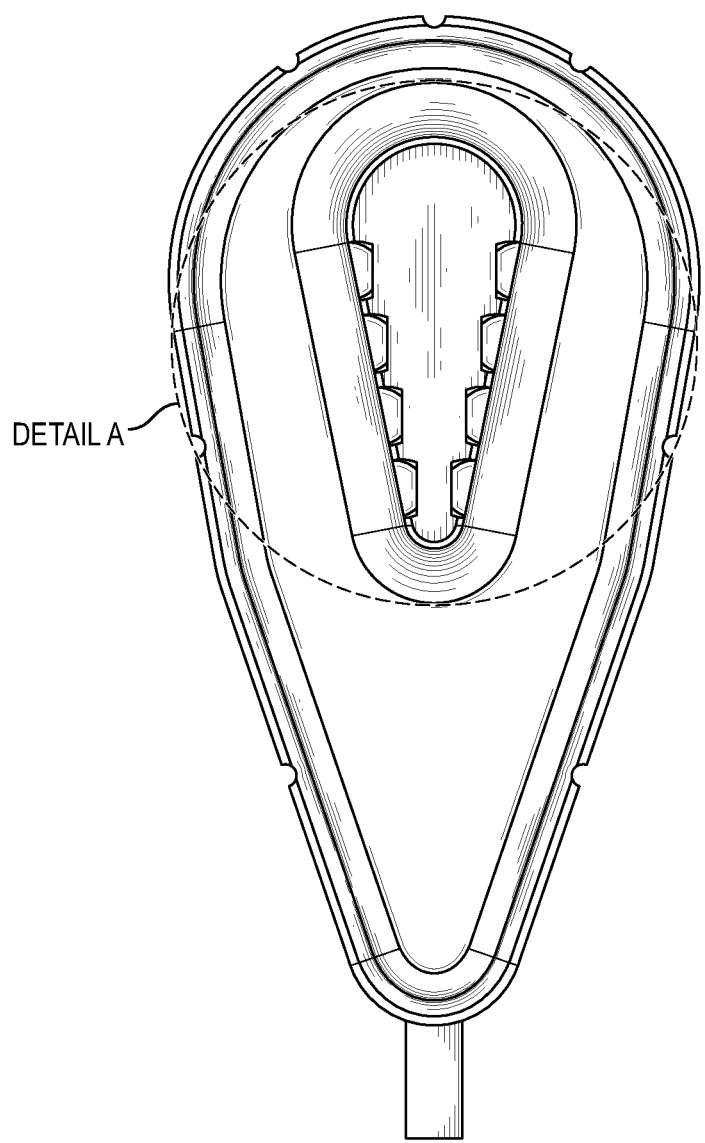
FIG. 3 shows an expanded view of a device having 8 one-way valves
Figure 3:
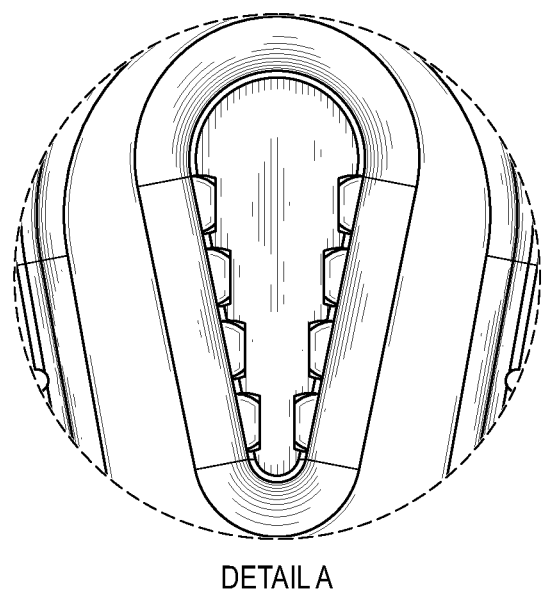
Figure 4:
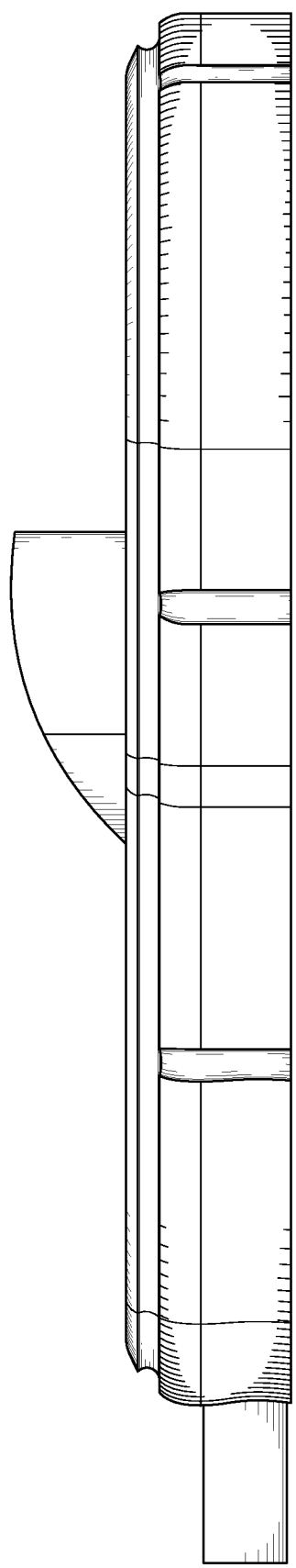
FIG. 4 shows another angle of a version of the device suitable for a male user.
Figure 5:
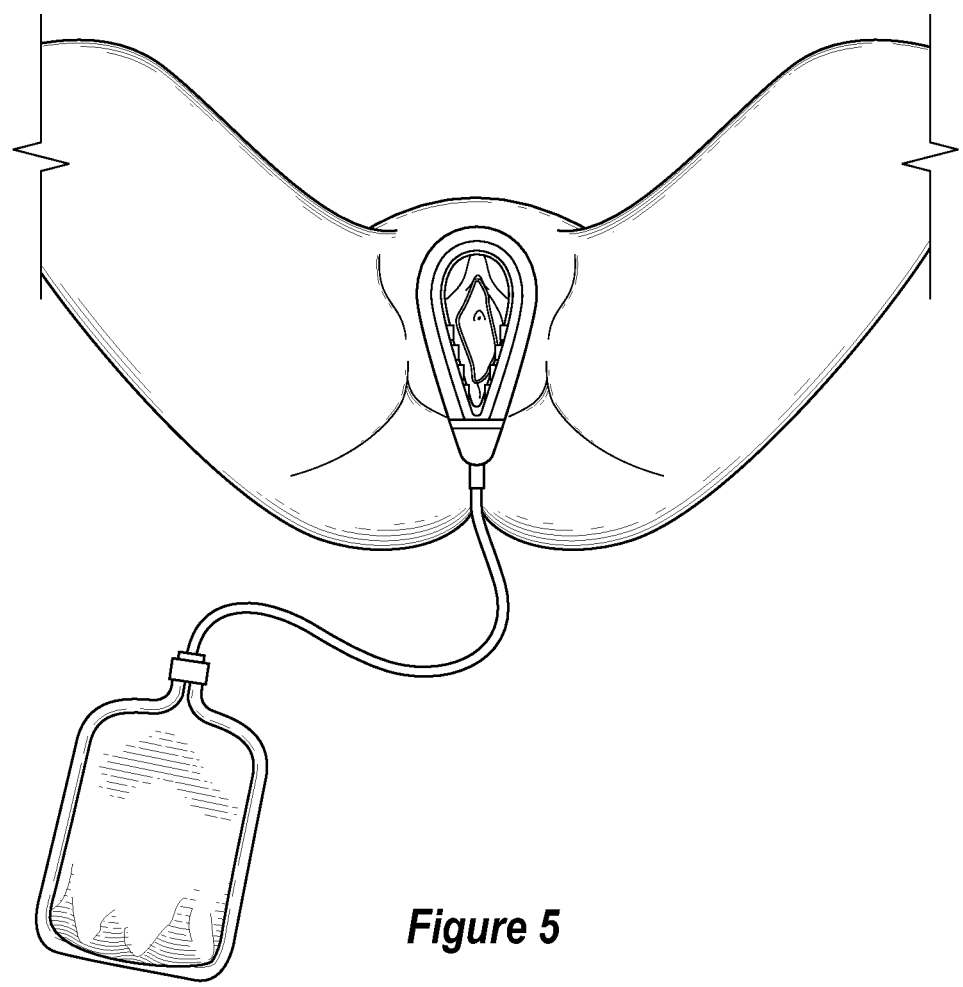
FIG. 5 shows the device in place on a female user.

The raised wall comprises one or more one way valves 104 configured for fluid to pass through the open cavity 100 into the interior of the closed cavity beneath the wall 103. FIG. 3 shows an expanded view of a device having 8 one-way valves. FIG. 4 shows another angle of a version of the device suitable for a male user.

A mechanism to secure the device to a user having a female urethal opening and a buttocks may be realasably attached or through one or more apertures, loops, or indentations 105. The open cavity 100 is configured to sealably encompass the female urethal opening with raised wall 101 firmly pressed against the user body. The proximate end 106 of the closed cavity beneath the wall 103 is configured to fit between a user's legs while the distal end 107 may extend at least partially over the buttocks. A two way valve 108 may be configured to empty fluid from the closed cavity when in an open position and can be connected to a bedside or other drainage device. Advantageously, the device is open via a slit in 102 so vaginal space is open to atmosphere allowing for aeration and ventilation. The slit in 102 may be configured so that its edges would adhere to labia majora edges.

On female device open system again allow for aeration such that female pelvic angle even at supine position will be about 30 degrees. Even in relatively immobile patients due to the angle of pelvis urine in the device travels straight down towards exit port which could be connected to bedside drainage device thereby further securing fluid move away from body quickly. This device could serve as a menses device also for female wherein a wicking agent could be placed on the inner cavity so that a female in standing or sitting position would have any extra fluid sequestered in inner cavity until it was drained. In that case the device would ensure dryness due to separation of wicking material not making contact with skin. In some embodiments the device may be added to a diaper so that if some leakeage occurred it would be wicked by diaper. The advantage would be not having to change diaper as frequently if at all.

What is claimed is:

1. A urine collection device comprising: an open cavity with a raised wall around the perimeter of the open cavity and a bottom connected to the raised wall; a closed cavity having an interior, wherein the closed cavity at least partially surrounds the open cavity and wherein the raised wall around the perimeter of the open cavity comprises a wall of the closed cavity and wherein said raised wall comprises one or more one way valves configured for fluid to pass through the open cavity into the interior of the closed cavity; a mechanism to secure the device to a user having a female urethal opening and a buttocks; wherein the open cavity is configured to sealably encompass the female urethal opening; and wherein the closed cavity is configured to fit between a user's legs and extend at least partially over the buttocks.

2. The urine collection device of claim 1 wherein the closed cavity further comprises a two way valve configured to empty fluid from the closed cavity when in an open position.

3. The urine collection device of claim 1 wherein the raised wall comprises two or more one way valves.

4. The urine collection device of claim 1 wherein the raised wall comprises three or more one way valves.

5. The urine collection device of claim 1 wherein the raised wall comprises four or more one way valves.

6. The urine collection device of claim 1 wherein the raised wall comprises five or more one way valves.

7. The urine collection device of claim 1 wherein the raised wall comprises six or more one way valves.

8. The urine collection device of claim 1 wherein the device is configured such that fluid passes through the one or more one way valves into the closed cavity via gravity when the user wearing the device is in an upright position.

9. The urine collection device of claim 1 wherein the device is configured such that fluid passes through the one or more one way valves into the closed cavity via gravity when the user wearing the device is in a standing position.

10. The urine collection device of claim 1 wherein the device is configured such that fluid passes through the one or more one way valves into the closed cavity via gravity when the user wearing the device is in a seated position.

11. The urine collection device of claim 1 wherein the device is configured such that fluid passes through the one or more one way valves into the closed cavity via gravity when the user wearing the device is in a horizontal position facing up.

12. The urine collection device of claim 1 wherein the device is configured such that fluid passes through the one or more one way valves into the closed cavity via gravity when the user wearing the device is standing, seated, or in a horizontal position facing up position.

13. The urine collection device of claim 1 wherein the device is in the shape of a tapered ellipse.

14. The urine collection device of claim 1 wherein the device comprises a material selected from rubber, latex, poly chi oroprene, nylon, polyethylene, polypropylene, elastomer, polyolefin, silicone, neoprene, or mixtures thereof.

15. The urine collection device of claim 1 wherein the interior of the closed cavity is configured to hold at least 400 cc of fluid.

16. The urine collection device of claim 1 wherein the mechanism to secure the device to the user is releasable.

17. The urine collection device of claim 1 wherein the mechanism to secure the device to the user is selected from the group consisting of tape, adhesive, straps, velcro, kellum grip, or combinations thereof.

18. The urine collection device of claim 1 wherein the mechanism to secure the device to the user comprises six or more fasteners proximate to the perimeter of the closed cavity.

19. The urine collection device of claim 1 further comprising a fluid level indicator.

20. The urine collection device of claim 1 wherein one or more surfaces of the device comprise an antimicrobial material, an antifungal material, a homeopathic material, and mixtures thereof.

* * * * *